United States Patent [19]  [11]  4,422,187
Zweymüller  [45]  Dec. 27, 1983

[54] SHANK FOR A JOINT ENDOPROSTHESIS

[75] Inventor: Karl Zweymüller, Vienna, Austria

[73] Assignee: Sulzer Brothers Limited, Winterthur, Switzerland

[21] Appl. No.: 221,254

[22] Filed: Dec. 30, 1980

[30] Foreign Application Priority Data

Jan. 14, 1980 [CH] Switzerland ................. 256/80

[51] Int. Cl.³ .................................. A61F 1/04
[52] U.S. Cl. .................. 3/1.913; 128/92 C; 92 CA
[58] Field of Search ................ 3/1.912, 1.913; 128/92 C, 92 CA

[56] References Cited

U.S. PATENT DOCUMENTS 3,024,758  3/1962  Dobelle ................ 128/92 CA
3,320,951  5/1967  Wittebol ............... 128/92 CA

FOREIGN PATENT DOCUMENTS 2839661  9/1979  Fed. Rep. of Germany ....... 3/1.912

OTHER PUBLICATIONS

Sloane, "A Simple Fixation Guide for Fracture Hips", Journal of Bone & Joint Surgery, vol. 27, Jul. 1945, p. 523.

Primary Examiner—Richard J. Apley
Assistant Examiner—David J. Isabella
Attorney, Agent, or Firm—Kenyon & Kenyon

[57] ABSTRACT

The prosthesis shank has a blade in which three predetermined points are designated. The points are formed as the centers of three bores which are formed in the shank in a triangular array. One bore is located on the longitudinal median axis while the other two bores are located on the pin axis. The points may also be determined by projections, depressions and or incisions. The designated points permit comparisons of x-ray pictures which are taken from time to time.

4 Claims, 1 Drawing Figure

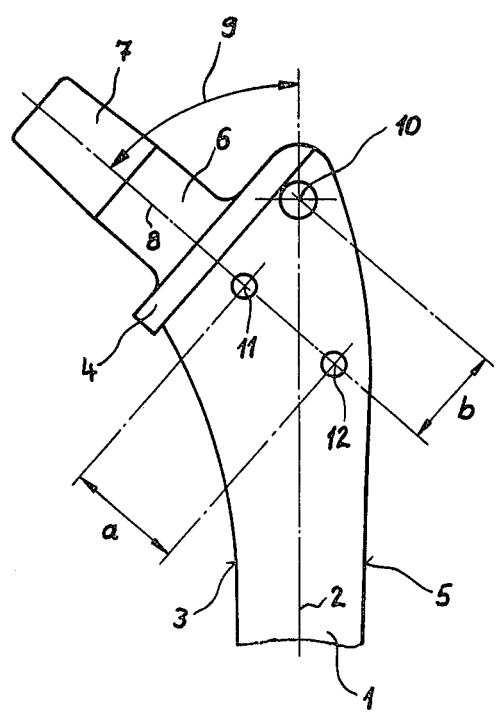

SHANK FOR A JOINT ENDOPROSTHESIS

This invention relates to a shank for a joint endoprothesis. More particularly, this invention relates to a shank for a hip joint prosthesis.

As is known, comparisons of x-ray pictures of implanted joint endoprosthesis taken at different times often presents difficulties. However, these comparisons are necessary in order to be able to discover displacements, for example a sinking in or a settling of an implant in a bone, as early as possible. The difficulties which have arisen are due, for example to different reproduction scales which arise between different x-ray pictures. Further, non-existing changes in the fit of a prosthesis may be simulated if the position of the limbs connected by a replacement joint relative to the direction at which the various pictures are taken is not the same.

Accordingly, it is an object of the invention to facilitate the comparison of x-ray pictures which are taken at different times of replacement joints.

Briefly, the invention provides a shank for a joint endoprosthesis which has a blade which widens from a distal end along a longitudinal median axis and a pin at a remote end which extends along a pin axis which intersects with the median axis. In accordance with the invention, the blade is provided with at least three predetermined points which are designated on the blade in a triangular array and at measured distances from each other.

The three points enclose a surface as large as possible and make it possible to establish in a simple manner, by measuring their image points on x-ray photographs, any changes in the reproduction scale and/or angle which the surface of the shank blade forms with the photographing direction. Moreover, if in a photograph taken immediately after implantation, the distances of the three points from characteristic points of the bone, for example from the upper edge of the greater trochanter or to the tip of the lesser trochanter in a hip joint prosthesis have been measured, the changes of position of the prosthesis in the bone can readily be determined in later photographs by measuring the distances.

In a particularly advantageous embodiment, the shank blade is provided with a plurality of bores with each bore having a center designating a respective one of the three points. In this case, if the photographing direction is not perpendicular to the surface of the shank blade an incorrect or at least a modified angular position between the shank blade and the photographing direction can be recognized at least approximately without measuring the image points due to an elliptical distortion which the bores would indicate.

It is also advantageous if one of the points lies on the longitudinal axis of the blade shank while two of the other points lie on the pin axis. In this case, the establishment of these axes on the photographs can be facilitated.

These and other objects and advantages of the invention will become more apparent from the following detailed description taken in conjunction with the accompanying drawing wherein:

The FIGURE illustrates a side view of a shank for a joint endoprosthesis in accordance with the invention.

Referring to the drawing, the shank, for example for a hip joint endoprosthesis, has a shank blade 1 at a lower end which widens from a distal end (not shown) along a longitudinal median axis 2. As indicated, the blade 1 widens in a conically upward direction as viewed with the conical shape being symmetrical to the median axis 2. In addition, a medial narrow side 3 of the blade 1 changes over via an arc to terminate within a collar 4. In like manner, the lateral narrow side 5 of the blade extends via an arc into the collar 4. In addition, the shank has a pin 7 at a remote end on the opposite side of the collar 4 from the blade 1. The pin 7 extends from a neck 6 which is integral with the collar 4 and tapers in an outwardly conical manner so as to receive a spherical joint head (not shown). The pin 7 extends along an axis 8 which intersects with the median axis 2 of the blade over an angle 9 which essentially corresponds to the angle between the neck and the axis of a the femur of a natural hip joint, for example 49°.

As shown, the blade 1 has three bores therein each of which has a center designating a predetermined point 10, 11, 12. These points 10, 11, 12 are disposed in a triangular array with the diameter of one bore defining the point 10 being of a diameter somewhat larger than the other bores which define the points 11, 12. As indicated, the point 10 lies on the longitudinal median axis 2 of the blade 1 while the points 11, 12 are disposed on the pin axis 8, one behind the other at an exactly measured distance a. In addition, the perpendicular distance b between the point 10 and the pin axis 8 is predetermined. The precise location of points 10, 11, 12 establish the size and position of the triangular surface enclosed by the points 10, 11, 12.

It is to be noted that the distance a and b can be selected at will. However, it is desirable to make these distances as large as possible to improve the relative precision for their measured values on x-ray pictures without weakening the mechanical properties of the shank, i.e. the strength of the shank.

It is to be noted that the invention is not limited to the illustrated embodiment either in the position of the points 10, 11, 12 on the axes 2, 8 nor in the manner in which the points 10, 11, 12 are designated. Thus, the points 10, 11, 12 may be designated by projections, simple depressions, or notch-like incisions.

By means of the points 10, 11, 12, a comparison of x-ray pictures which are taken at different times can be facilitated. In this regard, a measurement of the image points on the photographs indicate changes in the reproduction scale and/or angular position of the photographing direction to the surface of the shank blade. Further, by fixing these image points relative to characteristic points of a bone in which the shank is implanted immediately after implantation any changes in the position of the prosthesis shank in the bone that may have occurred over the course of time may be more easily discovered.

What is claimed is:

1. A shank for a joint endoprosthesis, said shank having a blade widening from a distal end along a longitudinal median axis and a pin at a remote end extending along a pin axis intersecting with said median axis, said blade having three circular bores disposed therein in a triangular array, each said bore having a center designating a predetermined point with one of said points on said longitudinal axis and two of said other points on said pin axis, said points being disposed at predetermined measured distances from each other whereby after implanting a measurement of said points on subsequently taken x-ray photographs indicate changes in the reproduction scale of an x-ray photograph and changes in angular position of the photographing direction to said blade.

2. A shank as set forth in claim 1 wherein said points are disposed on a side of said blade extending between the medial and lateral sides thereof.

3. A shank as set forth in claim 1 wherein one of said bores has a diameter larger than the other of said bores.

4. A shank as set forth in claim 1 wherein said bores on said pin axis are disposed on opposite sides of said longitudinal axis.

* * * * *